(12) United States Patent
Salzman et al.

(10) Patent No.: US 6,281,222 B1
(45) Date of Patent: Aug. 28, 2001

(54) COMPOSITIONS AND METHOD FOR TREATMENT OF ACETAMINOPHEN INTOXICATION

(75) Inventors: Andrew L. Salzman, Belmont; Jon Mabley, Beverly; Csaba Szabo, Glouster, all of MA (US)

(73) Assignee: Inotek Corporation, Beverly, MA (US)

( * ) Notice: Subject to any disclaimer, the term of this patent is extended or adjusted under 35 U.S.C. 154(b) by 0 days.

(21) Appl. No.: 09/641,249

(22) Filed: Aug. 17, 2000

Related U.S. Application Data

(60) Provisional application No. 60/149,839, filed on Aug. 19, 1999.

(51) Int. Cl.[7] ................................................. A61K 31/505
(52) U.S. Cl. ............................................................ 514/269
(58) Field of Search ............................................. 514/269

(56) References Cited

U.S. PATENT DOCUMENTS

| | | |
|---|---|---|
| 4,314,989 | 2/1982 | Rosen . |
| 5,260,340 | 11/1993 | Baranowitz et al. . |
| 5,474,757 | 12/1995 | Yang . |
| 5,637,315 | 6/1997 | Zern et al. . |
| 5,747,495 * | 5/1998 | Maeda et al. .................. 514/258 |

OTHER PUBLICATIONS

Miyamoto et al., Proc. Soc. For Exp. Biol. & Medicine, 211:366–373 (1996).
Laskin, et al., Toxicol. Appl. Pharmacol., 86:216–226 (1986).
Tirmenstein and Nelson, J. Biol. Chem., 265:3059–3065 (1990).
Jaeschke, J. Pharmacol. Exp. Ther., 255:935–941 (1990).
Crowell, et al., Am. J. Phys., 216:744–748 (1969).

* cited by examiner

*Primary Examiner*—Raymond Henley, III
(74) *Attorney, Agent, or Firm*—Mintz, Levin, Cohn, Ferris, Glovsky and Popeo, P.C.

(57) ABSTRACT

The invention provides compositions and methods for treatment of acetaminophen intoxication using an inhibitor of xanthine oxidase that does not induce superoxide radical formation when introduced into a subject. An example of a xanthine oxidase inhibitor that can be used according to the invention is AHPP.

25 Claims, 3 Drawing Sheets

COMPOSITIONS AND METHOD FOR TREATMENT OF ACETAMINOPHEN INTOXICATION

RELATED APPLICATIONS

This application claims priority to U.S. Ser. No. 60/149,839, filed Aug. 19, 1999. The contents of this application are incorporated by reference in their entire

FIELD OF THE INVENTION

The invention relates to compositions and methods for treating or preventing acetaminophen intoxication.

BACKGROUND OF THE INVENTION

Acetaminophen is a mild analgesic and anesthetic that is safe and effective when ingested in therapeutic doses. Overdoses of acetaminophen, however, can lead to long-term health problems and can even be fatal. For example, overdoses of acetaminophen can lead to acute liver failure which may be associated with multi-organ failure, nephrotoxicity and occasionally pancreatitis. Acetaminophen intoxication can also occur in individuals with, e.g., impaired hepatic function, renal disease, chronic alcoholism, or malnutrition.

Damage caused by high doses of acetaminophen can manifest itself by elevated serum levels of the liver enzymes aspartate transaminase (AST) and alanine aminotransferase (ALT).

SUMMARY OF THE INVENTION

The invention is based in part on the discovery that inhibitors of the enzyme xanthine oxidase (XO) can be used to treat acetaminophen poisoning in a subject.

Accordingly, in one aspect the invention provides a method of treating tissue injury associated with ingestion of acetaminophen in a subject by administering to a subject in need thereof a pharmaceutically effective amount an inhibitor of xanthine oxidase.

Also within the invention is a method of preventing inflammation in a subject by administering to a subject at risk thereof a pharmaceutically effective amount an inhibitor of xanthine oxidase, wherein the inhibitor does not form a superoxide radical when introduced in the subject.

In another aspect, the invention includes a method of suppressing undesired free radical formation by administering to a subject in need thereof a pharmaceutically effective amount of an inhibitor of xanthine oxidase, wherein the inhibitor does not form a superoxide radical when introduced into the subject.

In a further aspect, the invention provides a method of enhancing survival in a subject suffering from acetaminophen intoxication by administering an inhibitor of xanthine oxidase in an amount sufficient to prolong survival of the subject.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and are not intended to be limiting.

Other features and advantages of the invention will be apparent from the following detailed description and claims.

DETAILED DESCRIPTION OF THE INVENTION

Figure 1A:
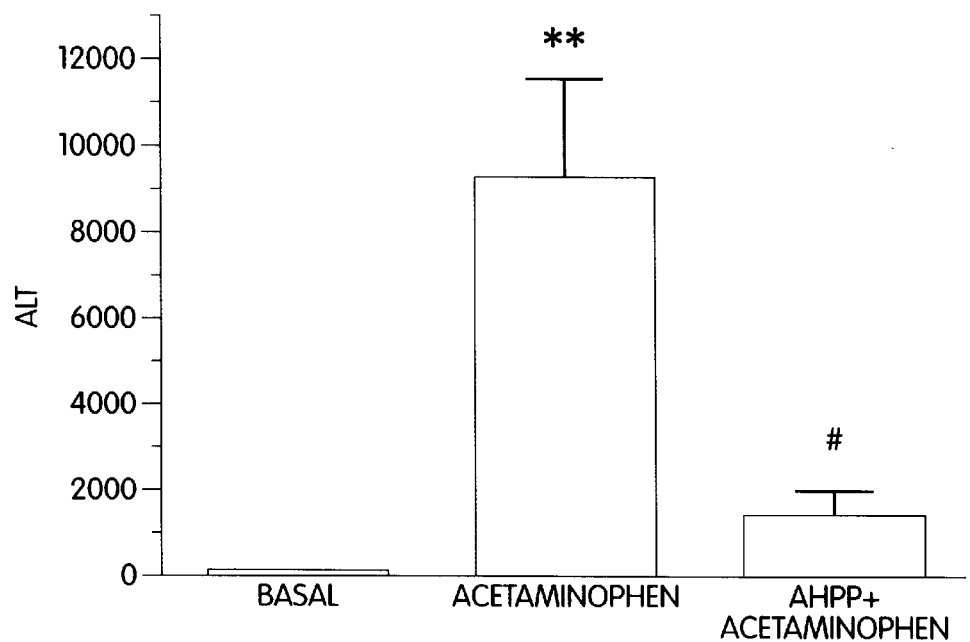
FIGS. 1A and 1B are graphs showing ALT (FIG. 1A) and AST (FIG. 1B) levels in vehicle-treated mice ("basal") and in rats treated with acetaminophen, or acetaminophen and AHPP.

The invention provides methods and compositions for treating symptoms and damage associated with ingestion of high levels, e.g., toxic levels, of acetaminophen (paracetamol) in a subject. The method includes administering to the subject an inhibitor of xanthine oxidase (XO) in an amount sufficient to alleviate the undesirable symptoms or to treat tissue damage associated with acetaminophen ingestion. Preferably, the inhibitor does not cause superoxide radical formation when introduced into the subject.

In some embodiments, the XO inhibitor is administered to a subject suffering from, or at risk for, symptoms associated with acetaminophen intoxication. As used herein, acetaminophen intoxication refers to a situation in which a subject has ingested, or is at risk for ingesting, an amount of acetaminophen sufficient to cause significant undesirable symptoms associated with the ingestion of acetaminophen. Symptoms of acetaminophen intoxication that occur within 12–14 hours of ingestion of an overdose of acetaminophen can include, e.g., nausea, vomiting, diaphoresis and anorexia.

The effect of the inhibitor in alleviating undesirable symptoms associated with acetaminophen ingestion can be monitored using art-recognized techniques for assaying the effect of acetaminophen on a subject. For example, the effect of the inhibitor can be determined by measuring levels of hepatic serum aspartate transaminase (AST) and alanine aminotransferase (ALT) in the subject. Lowering of AST and ALT serum levels in the subject after administration of the inhibitor indicates that the inhibitor is alleviating undesirable symptoms associated with acetaminophen ingestion.

In another aspect, the invention provides a method of suppressing undesired free radical formation in subject by administering to the subject a pharmaceutically effective amount of an inhibitor of xanthine oxidase that does not cause superoxide radical formation when introduced into the subject. In some embodiments, free radical formation is caused by ingestion of acetaminophen by the subject.

Also provided by the invention is a method of enhancing survival in a subject suffering from, or at risk for, acetaminophen intoxication. The method includes administering to a subject an XO inhibitor in an amount sufficient to prolong survival of the subject. In some embodiments, the subject has ingested, or is at risk for ingesting, a lethal dose of acetaminophen.

An example of a XO inhibitor that can be used in the methods disclosed herein is 4-Amino-6-hydroxypyrazolo[3,4-d]pyrimidine (AHPP). AHPP is described in e.g., Miyamoto et al., Proc. Society for Exp. Biology & Medicine 211:366–73, 1996. Additionally, AHPP is available from commercial vendors. Preferably, the XO inhibitor does not cause significant superoxide radical formation when introduced into a subject. More preferably, the inhibitor does not cause superoxide radical formation when introduced into a subject.

The subject in the methods described herein can be, e.g., a mammal, e.g., a human, mouse, rat, dog, cat, horse, cow, pig, or non-human primate. In some embodiments, the subject is a juvenile human, e.g., a subject less than 7 years of age, who has accidentally ingested on overdose of acetaminophen. In other embodiments, the subject is a human subject who has intentionally ingested an overdose of acetaminophen.

The term "pharmacologically effective amount" as used herein means that amount of a drug or pharmaceutical agent that will elicit the biological or medical response of a tissue, system, animal or human that is being sought by a researcher or clinician.

The inhibitor in the herein described methods can be administered prophylactically or therapeutically to the subject. When administered therapeutically, it can be administered, e.g., within 12 hours, 10, hours, 8 hours, 6 hours, 4 hours, 2 hours, 1 hour, or even 0.5 hour of ingestion of acetaminophen in the subject. Preferably, an XO inhibitor is administered as soon as possible after ingestion of acetaminophen.

The inhibitor can be administered in the methods described herein at a dose of from about 0.1 to about 500 mg/kg/day in the subject. For example, dosage ranges can be from e.g., 1–250 mg/kg, 2–100 mg/kg, 5–50 mg/kg, or 10–20 mg/kg daily, or every 2, 3, 4, or 5 days. A preferred dosage regimen is 10–150 mg/kg every 4 days. If desired, an XO inhibitor can be administered more than once to the subject. For example, successive administration of the XO inhibitor can be separated by 15 minutes, 30 minutes, 1 hour, 2 hours, 6 hours, 12 hours, or daily.

An XO inhibitor according to the invention can also be administered in conjunction with other treatment modalities for alleviating undesirable symptoms associated with acetaminophen intoxication. For example, an XO inhibitor can be administered along with N-acetyl cysteine.

Also provided by the invention is a method of preventing inflammation in a subject by administering to a subject at risk thereof a pharmaceutically effective amount an inhibitor of xanthine oxidase, wherein the inhibitor does not form a superoxide radical when introduced in the subject. The inhibitor can be, e.g., AHPP. In some embodiments, inflammation is caused by ingestion of a non-steroidal anti-inflammatory agent, e g., acetaminophen, by the subject.

Administration to the subject in the methods described herein can be, e.g., intravenous, intramuscular, subcutaneous, sublingual, oral, rectal or via aerosol delivery. The inhibitor can be administered as a pharmaceutical composition that includes a safe and therapeutically effective of an inhibitor of xanthine oxidase and a pharmaceutically effective carrier. Preferably, the pharmaceutical composition is formulated for treating symptoms associated with ingestion of high levels of acetaminophen in a subject. For example, the formulation can be formulated for treating symptoms associated with acetaminophen intoxication in the subject.

The compositions are preferably suitable for internal use and include an effective amount of a pharmacologically active compound of the invention, alone or in combination, with one or more pharmaceutically acceptable carriers. The compounds are especially useful in that they have very low, if any, toxicity.

In some embodiments, pharmaceutical compositions are tablets and gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and/or polyvinylpyrrolidone; if desired d) disintegrants, e.g., starches, agar, alginic acid or its sodium salt, or effervescent mixtures; and/or e) absorbents, colorants, flavors and sweeteners. Injectable compositions are preferably aqueous isotonic solutions or suspensions, and suppositories are advantageously prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. The compositions are prepared according to conventional mixing, granulating or coating methods, respectively, and contain about 0.1 to 75%, preferably about 0.1 to 50%, of the active ingredient.

Administration of the active compounds and salts described herein can be via any of the accepted modes of administration for therapeutic agents. These methods include systemic or local administration such as oral, nasal, parenteral, transdermal, subcutaneous, or topical administration modes. Depending on the intended mode of administration, the compositions may be in solid, semi-solid or liquid dosage form, such as, for example, injectables, tablets, suppositories, pills, time-release capsules, powders, liquids, suspensions, or the like, preferably in unit dosages. The compositions will include an effective amount of active compound or the pharmaceutically acceptable salt thereof, and in addition, and may also include any conventional pharmaceutical excipients and other medicinal or pharmaceutical drugs or agents, carriers, adjuvants, diluents, etc., as are customarily used in the pharmaceutical sciences.

Parental injectable administration is generally used for subcutaneous, intramuscular or intravenous injections and infusions. Injectables can be prepared in conventional forms, either as liquid solutions or suspensions or solid forms suitable for dissolving in liquid prior to injection. One approach for parenteral administration employs the implantation of a slow-release or sustained-released systems, which assures that a constant level of dosage is maintained, according to U.S. Pat. No. 3,710,795, which is incorporated herein by reference.

The dosage regimen utilizing an XO inhibitor is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter or arrest the progress of the condition.

Compounds of the present invention may be administered in a single daily dose, or the total daily dosage may be administered in divided doses of two, three or four times daily. Furthermore, preferred compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen. Other preferred topical preparations include creams, ointments, lotions, aerosol sprays and gels, wherein the concentration of active ingredient would range from 0.1% to 15%, w/w or w/v.

The compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices. Preferably, the carrier material does not form a superoxide radical when introduced into a subject.

The invention will be further illustrated in the non-limiting examples.

EXAMPLE 1
Effect of AHPP in Treating Effects of Acetaminophen Ingestion in an Animal Model System The efficacy of AHPP in treating effects of acetaminophen intoxication as a potential XO inhibitor was compared to allopurinol and N-acetylcysteine.

Male Balb/c mice (n=10 per group) were given 350 mg/kg acetaminophen per an intraperitoneal route. Although clinical intoxication occurs by an oral route, in this study, acetaminophen was administered in the animal model by an intraperitoneal (i.p.) route, because this technique insured a highly reproducible level of hepatic injury. Treatment with AHPP (as a suspension delivered by enteral gavage) was initiated at various timepoints relative to the parenteral administration of acetaminophen.

The difference in routes of administration of acetaminophen in the experimental model and clinical setting influence the rapidity of liver injury. In the experimental animal model, the exposure of the liver to acetaminophen is instantaneous, since parenteral administration ensures an immediate systemic uptake. In contrast, the effect of acetaminophen in the clinical setting is delayed, by as much as several hours, during which oral absorption occurs. These differences in the time of onset of acetaminophen exposure to the liver are relevant to the timing and efficacy of treatment regimens. In the clinical setting, treatment may be delayed several hours after oral ingestion of acetaminophen and still remain effective. In the experimental model (in which acetaminophen is administered by a parenteral route), the window of opportunity for effective therapy is considerably shorter, since hepatic exposure begins immediately upon parenteral administration of acetaminophen. Thus, the onset of protective activity is expected to occur after approximately 0.5–2 hours, depending on bioavailability.

Exposure to a toxic dose (350 mg/kg i.p. in saline) of acetaminophen produced a reproducible liver injury at 24 h, but not at 8 hours, characterized by elevation in serum transaminase and by histologic alterations of centrilobular necrosis. Upon gross examination at necropsy at 24 hours post-acetaminophen administration, livers were firm, hard, gray, mottled, and had occasional hematomas.

Figure 1B:
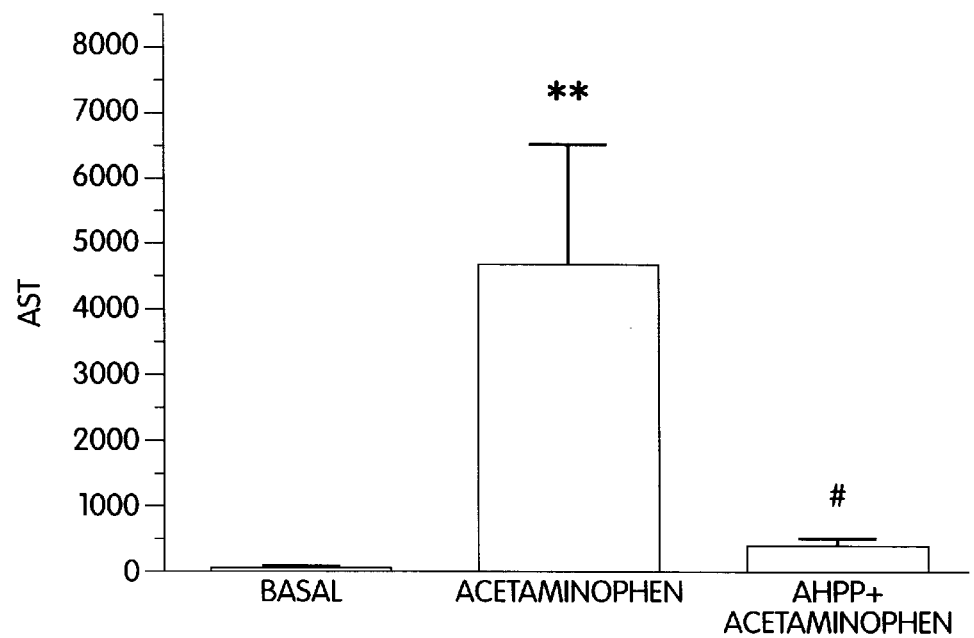

The effect of AHPP on the release of ALT and AST in plasma was examined. These parameters serve as standard indices of liver injury, and are known to increase in conjunction with acetaminophen-induced liver injury. The results are shown in FIGS. 1A and 1B. Shown is the effect of AHPP treatment when given simultaneously with acetaminophen on the degree of liver injury. The effect of AHPP is measured by the release of AST and ALT in rats. Acetaminophen was given at 350 mg/kg i.p., and AHPP was administered by enteral gavage as 50 mg/kg, followed by repeated enteral administrations of 50 mg/kg at 8 h and 16 h post-acetaminophen. N=7=8 animals per group; **$p<0.01$ represents significant increase in ALT (FIG. 1A) or AST (FIG. 1B) plasma levels in response to acetaminophen; #$p<0.05$ represents significant protection by AHPP.

As expected, acetaminophen injection (350 mg/kg i.p.) induced a marked increase in ALT and AST plasma levels, as measured at 24 h post-injection (FIGS. 1A and 1B). Treatment of rats with AHPP (50 mg/kg q8h per gavage) simultaneously with acetaminophen injection significantly reduced the degree of liver injury, as assessed by the release of ALT and AST.

A significant attenuation of the histological injury in the liver in response to AHPP treatment was also observed. Liver tissues were obtained from control rats, rats exposed to acetaminophen, or rats exposed to acetaminophen and AHPP. Scoring was performed by two independent investigators who were blinded to the treatment regimen. The following grading system was used: 0—normal liver, no signs of injury; 1—rare areas of centrilobular injury; 2—moderate injury involving many centrilobular areas; 3—extensive centrilobular necrosis; 4—massive hepatic injury involving all centrilobular areas and beyond. The median scores were as follows: control—0; Acetaminophen alone: 2.9; AHPP+Acetaminophen: 2.1 ($p<0.05$). Interobserver reliability exceeded 90%.

Figure 2:
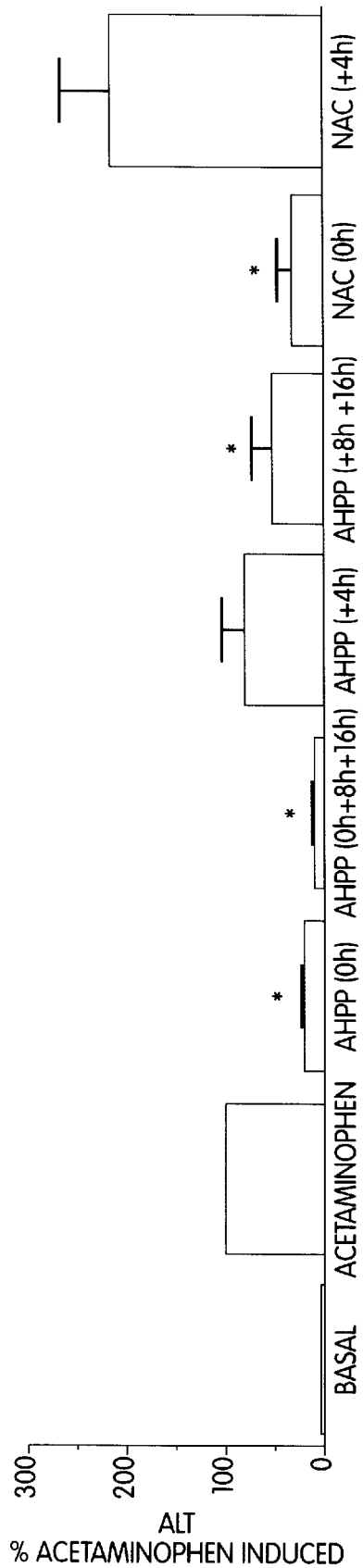
FIG. 2 is a graph showing changes in ALT levels over time in rats treated with vehicle, acetaminophen, acetaminophen and AHPP, and acetaminophen and NAC.

The effectiveness of AHPP when given at various frequencies and starting points of administration was also examined. Rats were exposed to vehicle or acetaminophen. Subsets of rats exposed to acetaminophen were additionally exposed to AHPP or N-acetyl-cysteine (NAC), a thiol compound used for treatment of acetaminophen intoxication. Serum ALT levels in rats were then examined The results are shown in FIG. 2. The bar graph in FIG. 2 depicts the effects of different frequencies and starting points of AHPP (or N-acetyl-cysteine) treatment on the toxicity of acetaminophen, as assessed by measurement of plasma ALT levels. The bars from the left to the right represent the following groups:

Basal (vehicle treated animals, no acetaminophen administration);

Acetaminophen: (350 mg/kg acetaminophen, administered at time 0; animals sacrificed 24 h later. ALT levels in the presence of acetaminophen, in the absence of AHPP or NAC treatment, are set at 100%);

AHPP (0 h)—ALT levels in rats poisoned with acetaminophen at time 0: AHPP treatment (50 mg/kg), administered, enterally via gavage at the time of acetaminophen injection) AHPP (0 h+8 H+16 h). In rats poisoned with acetaminophen at time 0: AHPP treatment (50 mg/kg), administered orally via gavage at the time of acetaminophen injection, followed by repeated enteral administrations at 8 h and 16 h post-acetaminophen at 50 mg/kg each time);

AHPP (4 h)—In rats poisoned with acetaminophen at time 0: AHPP treatment (50 mg/kg), administered enterally via gavage, at 4h post-acetaminophen;

AHPP (8 h+16 h)—In rats poisoned with acetaminophen at time 0: AHPP treatment: (50 mg/kg, administered enterally via gavage at 8 h post-acetaminophen, followed by a second treatment at 16 h post-acetaminophen;

NAC (0 h)–In rats poisoned with acetaminophen at time 0: N-acetyl-cysteine treatment (50 mg/kg), administered, enterally via gavage at the time of acetaminophen injection, and, NAC (4 h)–In rats poisoned with acetaminophen at time 0: NAC treatment (50 mg/kg), administered enterally via gavage, at 4 h post-acetaminophen.

N=7=8 animals per group; *p<0.05 represents significant protection against the acetaminophen-induced increases in ALT plasma levels by AHPP or NAC.

Administration of AHPP concurrently with, or subsequent to administration of acetaminophen lowered ALT levels in rats as compared to rats administered acetaminophen alone. AHPP appeared most effective when the start of administration was close in time to the administration of acetaminophen, and when the initial dosing was followed by additional AHPP treatments (in this case, at 8 h interval).

The effect of AHPP was reduced when administered at 4h post-acetaminophen and no supplemental doses were given. However, AHPP still showed significant protective effects when administered as late as 8 h after acetaminophen, and when a second dose of AHPP was given 16 hours after administering acetaminophen. This latter observation is significant, considering that a relatively short (24 h) protocol was used and the route of administration of AHPP was via gavage. These results indicate that the drug has sufficient enteral uptake.

In comparison, the same dose of N-acetyl-cysteine (50 mg/kg, administered enterally), while significantly protective in the co-treatment scenario, lost its protective effect when applied as a 4-h post-treatment. In fact, N-acetyl-cysteine actually exacerbated the degree of liver injury when given in the 4 h post-treatment scenario (FIG. 2).

The above data obtained with AHPP demonstrate that (1) AHPP advantageously compares to NAC as a hepatoprotective agent in acetaminophen intoxication, (2) AHPP is effective via an enteral delivery route; (3) AHPP is effective both as a co-treatment and in delayed post-treatment regimens.

EXAMPLE 2

Effect of AHPP on Prolonging Survival of in an Acetaminophen Animal Model

In order to assess the protective efficacy of AHPP on survival, the injury model was modified by increasing the period of fasting prior to acetaminophen exposure (350 mg/kg i.p.; n=8 animals per group) from 16 to 36 hours. Pilot studies revealed that this model created a rapidly fatal fulminant hepatic failure.

Figure 3:
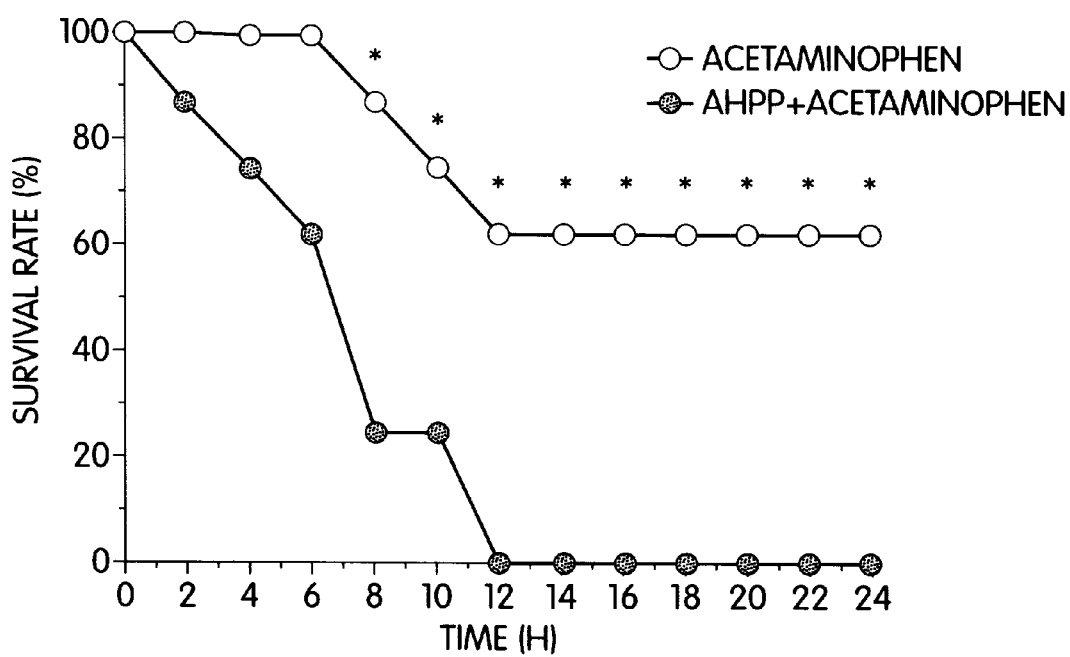
FIG. 3 is a graph showing survival over time in acetaminophen-intoxicated mice treated with AHPP or a control.

The results of a survival study are shown in FIG. 3. The graph in FIG. 3 depicts survival after severe acetaminophen intoxication in mice fasted for 36 hours. Animals were exposed to acetaminophen (350 mg/kg i.p.) and treated simultaneously with AHPP at a dose of 30 mg/kg q8h given by enteral gavage.

Acetaminophen injection induced lethality as early as 2 hours. By 8 hours, mortality rose to 75%. In contrast, treatment with AHPP given by gavage (30 mg/kg q8h) at the time of acetaminophen exposure was markedly protective. Therefore, AHPP dramatically prolonged survival.

EXAMPLE 3

Determination of the Effective AHPP Dose in Treating Symptoms Associated with Acetaminophen Ingestion The minimally effective dose of AHPP was examined. Criteria for an effective dose included ability to suppress liver injury and protect against acetaminophen-induced mortality. For liver injury, reducing the dose of AHPP to 10 mg/kg q8h per enteral gavage still exerted significant protective effects (n=7; p<0.01), as evidenced by an 89% reduction in serum ALT concentration (i.e., equivalent in efficacy to the 50 mg/kg dose utilized in the previous study, as shown in FIG. 2). An even greater reduction in the dose of AHPP to 3 mg/kg q8h per enteral gavage also resulted in a significant protection. Although the effect was only partial, ALT levels were reduced by 56±16% (n=8; p<0.05).

In order to validate the significance of the above mentioned reductions in serum transaminases, a dose response survival study was also performed. Dosages of both 3 and 10 mg/kg q8 of AHPP given by enteral gavage significantly protected against mortality at 8 hours. Survival rate was 25% in the vehicle treated group, and improved to 87% with 3 mg/kg and 10 mg/kg q8h doses. However, at 24 hours the lower dose (3 mg/kg q8h) lost its protective effect (0% survival in both the AHPP-treated and vehicle-treated groups), whereas as the 10 mg/kg q8h treated group maintained its protective effect (63% survival at 24 hours). For the survival studies, n=8–10 animals per group. These data demonstrate that AHPP protects against liver injury and mortality in a stringent model of acetaminophen intoxication. The effective dose range lays between 10 and 50 mg/kg of AHPP q8h per enteral gavage.

EXAMPLE 4

Toxicity of AHPP

Preliminary toxicity studies were performed with AHPP to estimate the expected therapeutic ratio of the compound. Enteral administration of AHPP up to 1000 mg/kg, did not result in mortality or behavioral or histological alterations in mice (n=8 animals per group at 1000, 500, and 300 mg/kg via enteral gavage followed for 24h and sacrificed at that time point), indicating that the therapeutic ratio of the compound is at least 1:30.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed:

1. A method of treating tissue injury associated with ingestion of acetaminophen in a subject, said method comprising administering to a subject in need thereof a pharmaceutically effective amount of an inhibitor of xanthine oxidase.

2. The method of claim 1, wherein said inhibitor does not cause superoxide radical formation when introduced into said subject.

3. The method of claim 1, wherein said inhibitor is 4-Amino-6-hydroxypyrazolo[3,4d]pyrimidine (AHPP).

4. The method of claim 1, wherein said tissue injury includes injury to liver tissue in said subject.

5. The method of claim 1, wherein said subject is a human.

6. The method of claim 1, wherein said inhibitor is administered prophylactically to said subject.

7. The method of claim 1, wherein said inhibitor is administered therapeutically to said subject.

8. The method of claim 7, wherein said inhibitor is administered within 12 hours of ingestion of acetaminophen in said subject.

9. The method of claim 7, wherein said inhibitor is administered within 8 hours of ingestion of acetaminophen in said subject.

10. The method of claim 7, wherein said inhibitor is administered within 4 hours of ingestion of acetaminophen in said subject.

11. The method of claim 7, wherein said inhibitor is administered within 2 hours of ingestion of acetaminophen in said subject.

12. The method of claim 7, wherein said inhibitor is administered within 1 hour of ingestion of acetaminophen in said subject.

13. The method of claim 1, wherein said administration is administered by a route selected from intravenous, intramuscular, subcutaneous, sublingual, oral, rectal or aerosol delivery.

14. The method of claim 1, wherein said administration is intravenous.

15. The method of claim 1, wherein said administration is oral.

16. The method of claim 1, wherein said inhibitor is administered at a dose of from about 0.1 to about 500 mg/kg/day in said subject.

17. The method of claim 1, further comprising administering said agent a second time to said subject, wherein the second administration is at least about 15 minutest after the first administration of said agent.

18. A method of preventing inflammation in a subject, said method comprising administering to a subject at risk thereof a pharmaceutically effective amount an inhibitor of xanthine oxidase, wherein said inhibitor does not cause superoxide radical formation when introduced into said subject.

19. The method of claim 18, wherein said inflammation is caused by ingestion of a non-steroidal anti-inflammatory agent in said subject.

20. The method of claim 18, wherein said inhibitor is AHPP.

21. A method of suppressing undesired free radical formation in subject, said method comprising administering to a subject in need thereof a pharmaceutically effective amount of an inhibitor of xanthine oxidase, wherein said inhibitor does not cause superoxide radical formation when introduced into said subject.

22. A method for treating acetaminophen intoxication in a subject, said method comprising administering to said subject a pharmaceutically effective amount an inhibitor of xanthine oxidase, wherein said inhibitor does not cause superoxide radical formation when introduced in said subject.

23. The method of claim 22, wherein said inhibitor is AHPP.

24. The method of claim 22, wherein said subject is a human.

25. A method of enhancing survival in a subject subjected to acetaminophen intoxication, said method comprising administering to a subject an amount of AHPP sufficient to prolong survival of said subject.

* * * * *